United States Patent
Shibata et al.

(10) Patent No.: US 8,734,340 B2
(45) Date of Patent: May 27, 2014

(54) METHOD, APPARATUS AND SYSTEM FOR PROVIDING HEALTHCARE SUPPORT BY MESSAGE BASED COMMUNICATION TO HEALTHCARE SUPPORT TERMINALS

(75) Inventors: Mariko Shibata, Yokohama (JP); Yoichi Takada, Otawara (JP); Motoji Haragashira, Utsunomiya (JP); Kozo Sato, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 875 days.

(21) Appl. No.: 11/022,784

(22) Filed: Dec. 28, 2004

(65) Prior Publication Data

US 2005/0148831 A1 Jul. 7, 2005

(30) Foreign Application Priority Data

Jan. 6, 2004 (JP) .................... 2004-001185
Nov. 30, 2004 (JP) .................... 2004-347669

(51) Int. Cl.
*A61B 5/00* (2006.01)
*G06F 19/00* (2011.01)
*G08B 1/08* (2006.01)

(52) U.S. Cl.
CPC .......... *G06F 19/3425* (2013.01); *G06F 19/345* (2013.01); *G06F 19/34* (2013.01); *G06F 19/3418* (2013.01); *A61B 5/0022* (2013.01); *A61B 5/0002* (2013.01); *A61B 5/7282* (2013.01); *G08B 1/08* (2013.01); *A61B 2505/01* (2013.01); *A61B 2505/07* (2013.01); *Y10S 128/92* (2013.01)
USPC .............. 600/300; 705/2; 705/3; 340/539.12; 340/539.16; 340/539.18; 128/920

(58) Field of Classification Search
CPC ........... G06F 19/3445; G06F 19/3425; G06F 19/3418; G06Q 50/22; A61B 5/0002; A61B 5/0022; A61B 5/002; A61B 5/72; A61B 5/7282
USPC .......... 600/300–301, 201; 128/903–905, 920; 705/2–3; 340/539.12, 539.16, 539.18
See application file for complete search history.

(56) References Cited

U.S. PATENT DOCUMENTS 5,128,979 A * 7/1992 Reich et al. ............... 379/40
5,576,952 A * 11/1996 Stutman et al. .......... 600/300

(Continued)

FOREIGN PATENT DOCUMENTS

JP 9-101998 4/1997
JP 9-313452 12/1997

(Continued)

OTHER PUBLICATIONS

Office Action issued Feb. 8, 2011, in Japanese Patent Application No. 2004-347669 (with English translation).

*Primary Examiner* — Bill Thomson
*Assistant Examiner* — Marie Archer
(74) *Attorney, Agent, or Firm* — Oblon, Spivak, McClelland, Maier & Neustadt, L.L.P.

(57) ABSTRACT

A patient terminal can communicate with doctor terminals and a center terminal via a communication network. The patient terminal acquires vital data from a measuring device with a receiving unit. A control unit determines whether the vital data contains an abnormal value and the necessity of messaging depending on the presence or absence of a manual messaging request with a message button and selects the doctor terminal or the center terminal. When it is determined that messaging is necessary, the control unit makes a communication unit call the selected terminal.

12 Claims, 12 Drawing Sheets

(56) References Cited

U.S. PATENT DOCUMENTS

| | | | |
|---|---|---|---|
| 5,942,986 A * | 8/1999 | Shabot et al. | 340/7.29 |
| 6,057,758 A * | 5/2000 | Dempsey et al. | 340/539.12 |
| 6,221,009 B1 * | 4/2001 | Doi et al. | 600/300 |
| 6,234,964 B1 | 5/2001 | Iliff | |
| 6,302,844 B1 * | 10/2001 | Walker et al. | 600/300 |
| 6,669,631 B2 | 12/2003 | Norris et al. | |
| 6,696,956 B1 * | 2/2004 | Uchida et al. | 340/573.1 |
| 7,027,402 B2 * | 4/2006 | Hedden | 370/238 |
| 7,149,774 B2 * | 12/2006 | Zellner et al. | 709/203 |
| 7,264,590 B2 * | 9/2007 | Casey et al. | 600/300 |
| 7,395,046 B2 * | 7/2008 | Hossain et al. | 455/404.1 |
| 2002/0019584 A1 * | 2/2002 | Schulze et al. | 600/300 |
| 2003/0046421 A1 * | 3/2003 | Horvitz et al. | 709/238 |
| 2004/0034284 A1 * | 2/2004 | Aversano et al. | 600/300 |
| 2004/0068197 A1 | 4/2004 | Sarel | |

FOREIGN PATENT DOCUMENTS

| | | |
|---|---|---|
| JP | 11-276444 | 10/1999 |
| JP | 2001-190504 A | 7/2001 |
| JP | 2001-312782 | 11/2001 |
| JP | 2002-143100 A | 5/2002 |
| JP | 2002-230672 | 8/2002 |
| JP | 2002-279077 A | 9/2002 |
| JP | 2002-291879 | 10/2002 |

* cited by examiner

METHOD, APPARATUS AND SYSTEM FOR PROVIDING HEALTHCARE SUPPORT BY MESSAGE BASED COMMUNICATION TO HEALTHCARE SUPPORT TERMINALS

CROSS-REFERENCE TO RELATED APPLICATIONS

This application is based upon and claims the benefit of priority from prior Japanese Patent Applications No. 2004-001185, filed Jan. 6, 2004; and No. 2004-347669, filed Nov. 30, 2004, the entire contents of both of which are incorporated herein by reference.

BACKGROUND OF THE INVENTION

1. Field of the Invention

The present invention relates to a method of providing a healthcare support service for making home care possible, a communication unit, and system and apparatus for providing healthcare support.

2. Description of the Related Art

The nucleus of the disease structure of advanced countries has shifted from acute diseases such as infection to chronic diseases called life-style related diseases with an improvement in living level. Typical chronic diseases include diabetes. An increase in such chronic diseases requires home care for supporting long-term therapy to combine social life and therapy.

As part of the measures, it is desired to be able to monitor patient's vital data and automatically inform medical institutions etc. of it in response to the aggravation in disease or to be able to consult doctors etc. online when patients feel uneasy about their health. For this purpose, for example, a system disclosed in JP-A-2002-291879 is proposed.

In environment in which the foregoing system is used, however, patients can easily access medical institutions without going out. Accordingly, the number of accesses to medical institutions will increase, producing the possibility of applying excess loads onto doctors who answer the accesses.

BRIEF SUMMARY OF THE INVENTION

Under these circumstances, it has been desired to make it possible to provide home therapy while reducing loads on doctors.

According to a first aspect of the present invention, there is provided a method of providing a healthcare support service with a healthcare support apparatus connectable to a plurality of providing-side terminals via a communication network. The method includes the steps of: acquiring patient's vital data; determining the necessity of messaging from the vital data; and selecting a destination terminal from the plurality of providing-side terminals according to the vital data and predetermined selecting conditions.

According to a second aspect of the invention, there is provided a method of providing a healthcare support service by a healthcare support system including a patient terminal, a plurality of providing-side terminals, and a healthcare support apparatus connectable to the terminals. The patient terminal acquires patient's vital data and transmits the vital data to the healthcare support apparatus. The healthcare support apparatus acquires the vital data transmitted from the patient terminal via the communication network, determines the necessity of messaging from the vital data, and selects a destination terminal from the plurality of providing-side terminals according to the vital data and predetermined selecting conditions.

According to a third aspect of the present invention, there is provided a method of providing a healthcare support service with a communication unit used as a patient terminal in a healthcare support system including a patient terminal, a plurality of providing-side terminals, and a healthcare support apparatus connectable to the terminals. The method includes the step of acquiring patient's vital data and the step of transmitting the vital data to the healthcare support apparatus.

According to a fourth aspect of the present invention, there is provided a healthcare support apparatus connectable to a plurality of providing-side terminals via a communication network. The apparatus includes an acquisition unit configured to acquire patient's vital data, a first determination unit configured to determine the necessity of messaging from the vital data, and a selection unit configured to select a destination terminal from the plurality of providing-side terminals according to the vital data and predetermined selecting conditions.

According to a fifth aspect of the present invention, there is provided a healthcare support system including a patient terminal, a plurality of providing-side terminals, and a healthcare support apparatus connectable to the terminals. The patient terminal includes a unit configured to acquire patient's vital data and a unit configured to transmit the vital data to the healthcare support apparatus. The healthcare support apparatus includes an acquisition unit configured to acquire the vital data transmitted from the patient terminal via the communication network, a determination unit configured to determine the necessity of messaging from the vital data, and a selection unit configured to select a destination terminal from the plurality of providing-side terminals according to the vital data and predetermined selecting conditions.

According to a sixth aspect of the present invention, there is provided a communication unit used as a patient terminal in a healthcare support system including a patient terminal, a plurality of providing-side terminals, and a healthcare support apparatus connectable to the terminals. The communication unit includes a unit configured to acquire patient's vital data and a unit configured to transmit the vital data to the healthcare support apparatus.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Embodiments of the present invention will be described with reference to the drawings.

First Embodiment

Figure 1:
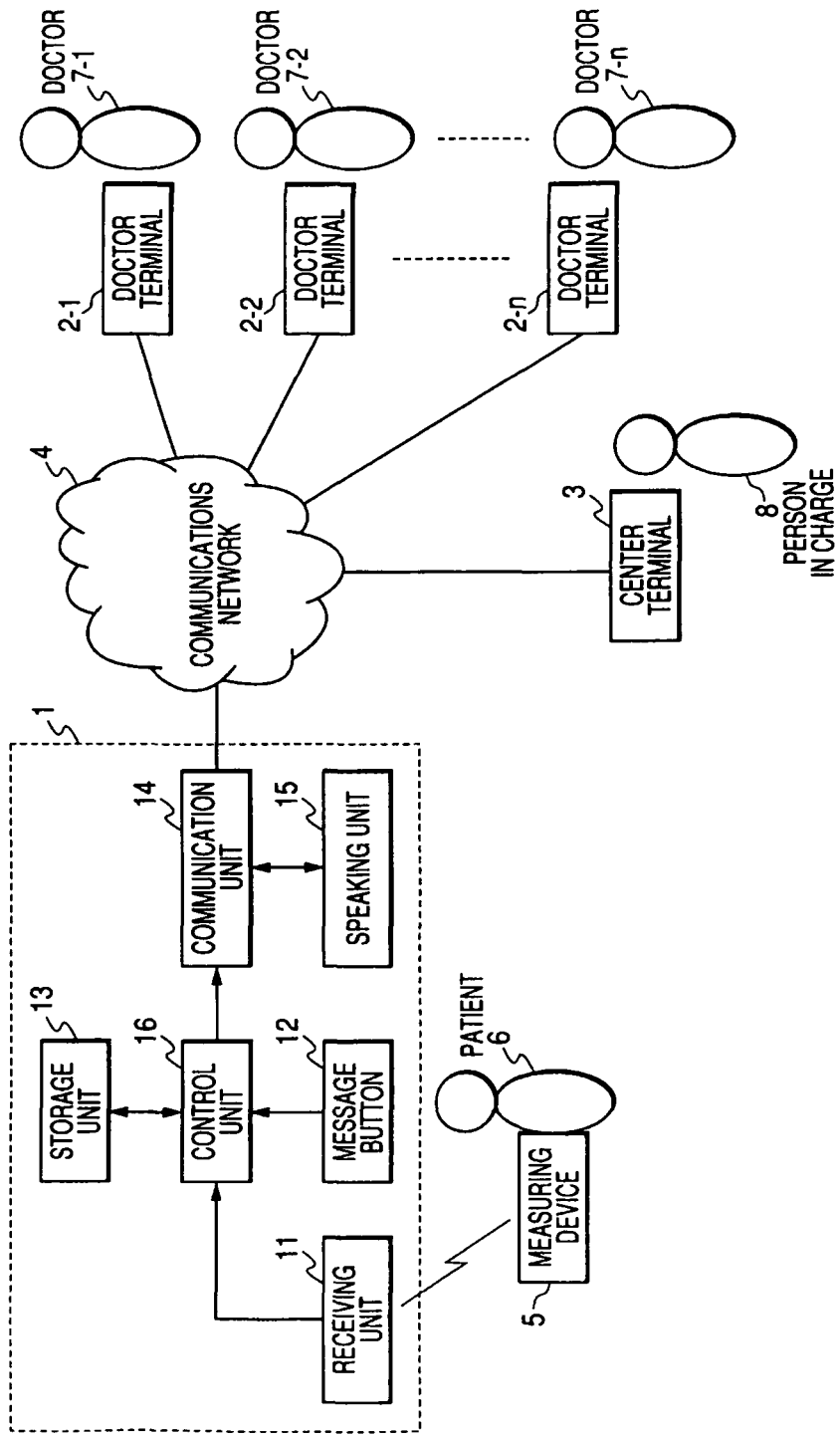
FIG. 1 is a block diagram showing the structure of a healthcare support system according to a first embodiment of the present invention.

FIG. 1 is a block diagram showing the structure of a healthcare support system according to a first embodiment of the present invention.

As shown in FIG. 1, the healthcare support system according to the first embodiment includes a patient terminal 1, doctor terminals 2-1 to 2-n, and a center terminal 3, each of which is connected to a communication network 4. The healthcare support system provides a healthcare support service capable of responding to a message from the patient terminal 1 by using the doctor terminals 2-1 to 2-n and the center terminal 3. Accordingly, the doctor terminals 2-1 to 2-n and the center terminal 3 are terminals on the side that provides the service.

The patient terminal 1 is one of the forms of the healthcare support apparatus according to the invention. The patient terminal 1 includes a receiving unit 11, a message button 12, a storage unit 13, a communication unit 14, a speaking unit 15, and a control unit 16.

The receiving unit 11 receives vital data transmitted from a measuring device 5. The measuring device 5 is mounted to a patient 6 who is the user of the patient terminal 1 at all times or at a predetermined timing. The measuring device 5 measures the vital data of the patient 6. The vital data indicates the condition of the body, such as body temperature, blood pressure, pulse, blood-sugar level, and blood oxygen level. The receiving unit 11 outputs the received vital data.

The message button 12 is depressed when the patient 6 desires to give a message to a medical institution. The message button 12 outputs a depression signal when depressed.

The storage unit 13 temporarily stores various information including vital data. The storage unit 13 stores information necessary to give a message to medical institutions.

The communication unit 14 performs communication processing for achieving communication via the communication network 4.

The speaking unit 15 includes a transmitter microphone and a receiver speaker. The speaking unit 15 is used when the patient 6 sends a voice message.

The control unit 16 is achieved by, for example, a CPU executing an application program. The control unit 16 performs the later-described processing for allowing the patient terminal 1 to send a message.

The doctor terminals 2-1 to 2-n are used by doctors 7-1 to 7-n, respectively. The doctor terminals 2-1 to 2-n have the function of receiving vital data via the communication network 4 and displaying the contents of the vital data. The doctor terminals 2-1 to 2-n also have the function of allowing the doctors 7-1 to 7-n to send a voice message via the communication network 4. When there is no need to differentiate the doctor terminals 2-1 to 2-n and the doctors 7-1 to 7-n, individually, the doctor terminal is expressed as "doctor terminal 2" and the doctor is expressed as "doctor 7" in the following description.

The center terminal 3 is used by a person in charge 8 who serves as an assistant of the doctor 7. The person in charge 8 may be a nurse or a stuff who belongs to the same medical institution as that of the doctor 7 or a person who does not belong to the medical institution. The person who does not belong to the medical institution includes, for example, employees of intermediary service sectors and employees of public health authorities. The center terminal 3 has the function of receiving the vital data via the communication network 4 and displaying the contents of the vital data. The center terminal 3 also has the function of allowing the person in charge 8 to send a voice message via the communication network 4.

The communication network 4 includes cable communication networks, such as a public switched telephone network (PSTN), an integrated services digital network (ISDN), a digital subscriber line (DSL) network, and an optical communication network, and a wireless communication networks, such as a personal digital cellular (PDC) network and personal handyphone system (PHS) network, alone or in combination.

The patient terminal 1 is lent to the patient 6 by a medical institution etc. The patient terminal 1 may be a general personal computer in which software is installed or which uses software via the Internet, thereby achieving the function of the patient terminal 1.

The storage unit 13 of the patient terminal 1 stores call information and order information. The call information includes telephone numbers for calling the doctor terminals 2-1 to 2-n and the center terminal 3. The order information includes an order to select a destination terminal from the doctor terminals 2-1 to 2-n.

Figure 2:
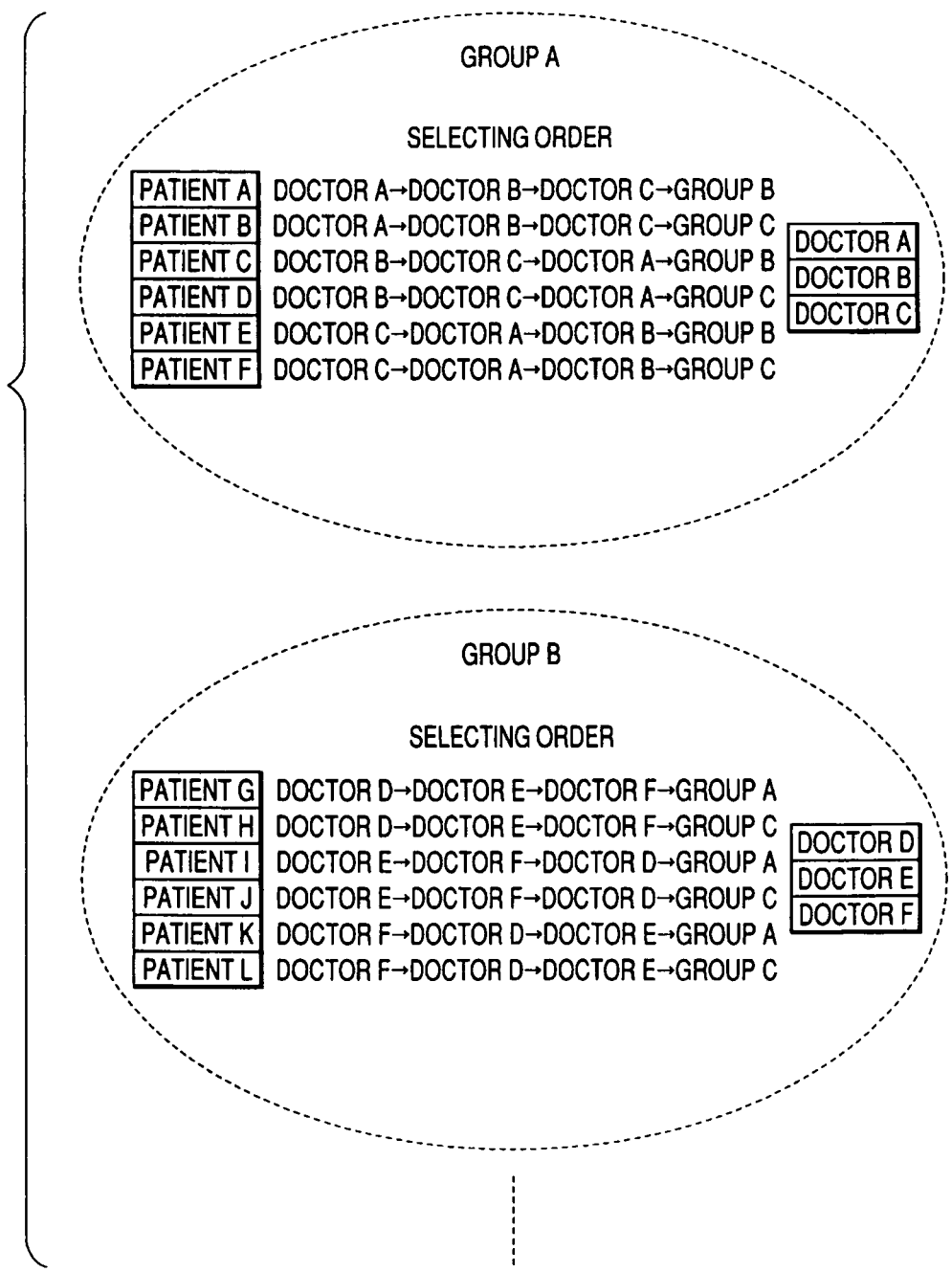
FIG. 2 is a diagram of an example of the contents of order information stored in the storage unit of FIG. 1.

The order in the order information may be determined freely by the operator of the system (e.g., a medical institution or an intermediary service sector). However, it is determined as shown in FIG. 2. Specifically speaking, patients and doctors are assigned to any of multiple groups. Selecting order is determined for each patient such that doctors who belong to the same group as the patient occupy an upper order. However, the selecting orders of the patients are differentiated as much as possible so that specific doctors concentrate on the upper order. For example, patients A to F and doctors A to C are assigned to group A. The upper order of the selecting order of the patients A to F is occupied by the doctors A to C in group A. Doctors in the order lower than the doctors A to C are assigned to another group.

Criteria for grouping patients may be a single or combination of address, age, seriousness, symptoms, complications, the order of application, etc. The grouping of patients may reflect patient's intention. It is desirable that doctors have competence of a certain level or more so as not to cause inequity among patients.

Figure 3:
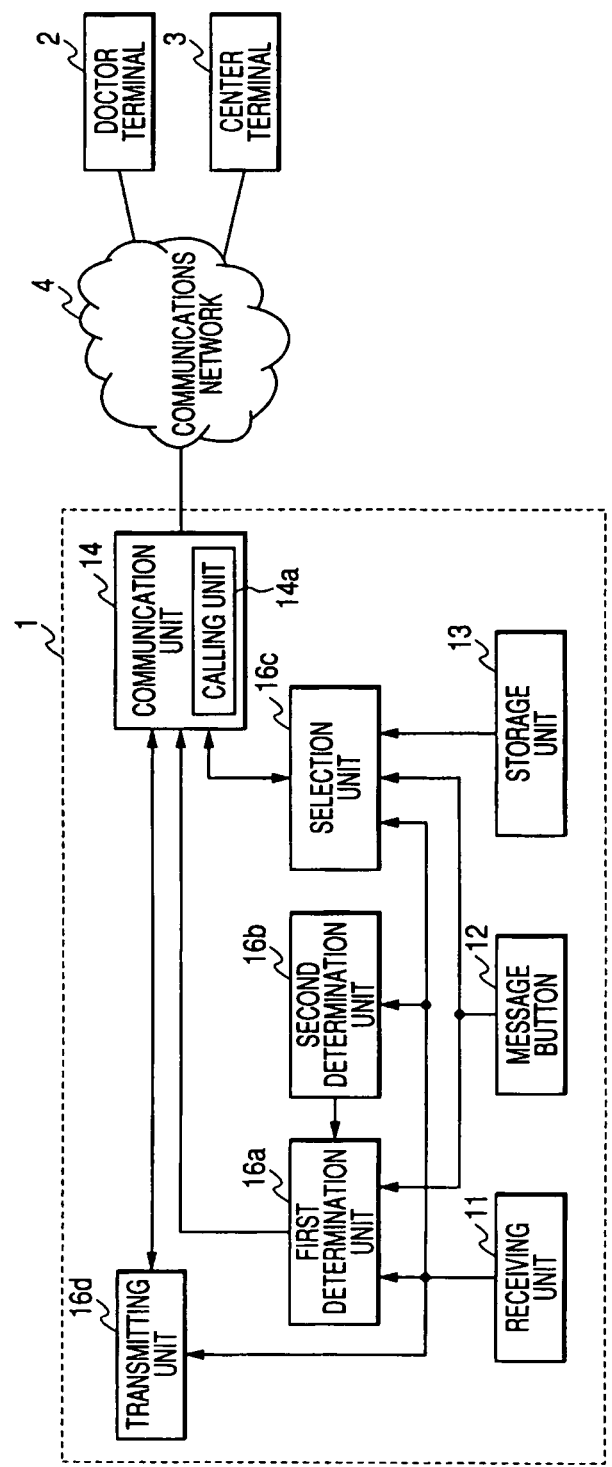
FIG. 3 is a block diagram showing the function of the patient terminal in FIG. 1.

FIG. 3 is a block diagram showing the function of the patient terminal 1 in FIG. 1. The same components in FIG. 3 as those of FIG. 1 are given the same reference numerals and their detailed description will be omitted.

A first determination unit 16a, a second determination unit 16b, a selection unit 16c, and a transmitting unit 16d of FIG. 3 are each achieved as one of the functions of the control unit 16.

The second determination unit 16b determines whether or not vital data outputted from the receiving unit 11 includes an abnormal value. The first determination unit 16a determines the necessity of messaging according to the vital data outputted from the receiving unit 11, the output state of a depression signal from the message button 12, and the determination of the second determination unit 16b. The selection unit 16c selects a destination terminal according to the vital data outputted from the receiving unit 11, the output state of the depression signal from the message button 12, and order information stored in the center terminal 3. The transmitting unit 16d transmits the vital data outputted from the receiving unit 11 to the destination terminal.

The communication unit 14 includes a calling unit 14a. The calling unit 14a calls a destination terminal selected by the selection unit 16c.

Then the operation of the healthcare support system with such a structure will be described.

Figure 4:
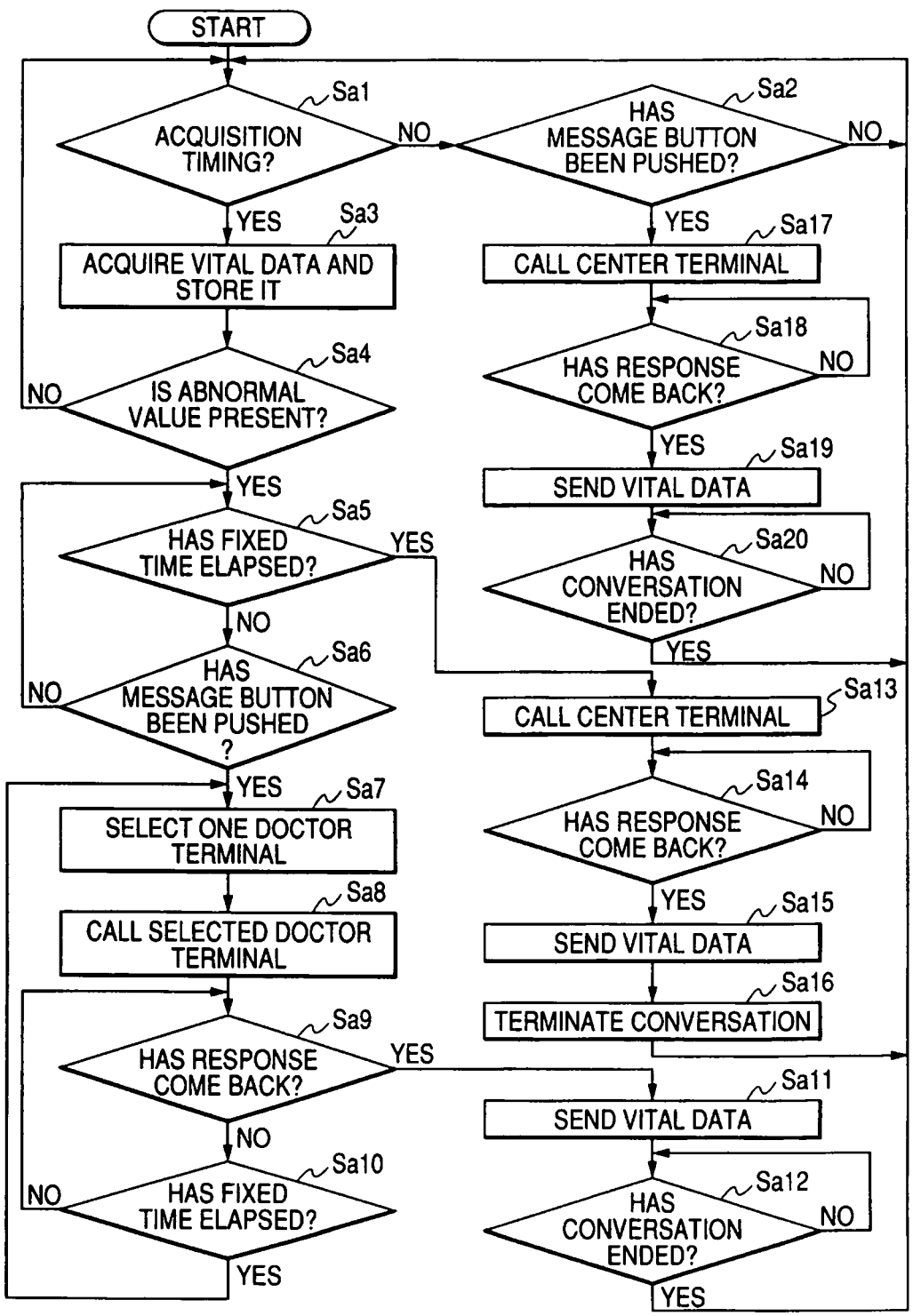
FIG. 4 is a flowchart for the procedure of the control unit in FIG. 1.

Upon activation of the patient terminal 1, the control unit 16 starts the processing shown in FIG. 4.

In steps Sa1 and Sa2, the control unit 16 waits for a timing to acquire vital data (hereinafter, referred to as an acquisition timing) or the depression of the message button 12. The acquisition timing may be determined freely or, for example, at regular intervals.

When the acquisition timing has come, the control unit 16 proceeds from step Sa1 to step Sa3. In step Sa3, the control unit 16 acquires the vital data received by the receiving unit 11 and stores the vital data in the storage unit 13. Subsequently, in step Sa4, the control unit 16 determines whether or not the obtained vital data contains an abnormal value. The determination is made by determining whether or not the value in the vital data is within a predetermined normal range. When no abnormal value is contained, the control unit 16 returns from step Sa4 to the standby mode in steps Sa1 and Sa2.

In contrast, when the vital data contains an abnormal value, the control unit 16 proceeds from step Sa4 to the standby mode of steps Sa5 and Sa6. In the standby mode of steps Sa5 and Sa6, the control unit 16 waits for a lapse of a fixed time after entry to the standby mode or the depression of the message button 12.

When the message button 12 is depressed before the lapse of a fixed time, the control unit 16 proceeds from step Sa6 to step Sa7. In step Sa7, the control unit 16 selects one of the doctor terminals 2-1 to 2-n according to the order information stored in the storage unit 13. When all doctor terminals in the same group have been selected and a doctor terminal to be selected next is designated by group, the control unit 16 selects one of the doctor terminals in the designated group as a destination terminal in accordance with a predetermined condition (e.g., at random). In step Sa8, the control unit 16 instructs the communication unit 14 to call the foregoing selected destination terminal. The control unit 16 then moves to a standby mode in steps Sa9 and Sa10. In steps Sa9 and Sa10, the control unit 16 waits for a response to the call or a lapse of a fixed time after entering the standby mode.

When no response is given within a fixed time, the control unit 16 returns from step Sa10 to step Sa7, wherein the control unit 16 selects another doctor terminal as a destination terminal and tries calling. When the destination terminal responds to the call into connection via the communication network 4, the control unit 16 proceeds from step Sa9 to step Sa11. In step Sa11, the control unit 16 transmits the vital data stored in the storage unit 13 in step Sa3 to the communication network 4. The vital data is thus sent to the destination terminal via the communication network 4. The doctor terminals 2-1 to 2-n have the function of receiving vital data via the communication network 4 and displaying the contents of the vital data. Accordingly, the contents of the vital data are displayed on the destination terminal, so that a doctor who uses the destination terminal can check the condition of the originating patient 6. The doctor terminals 2-1 to 2-n also have the function of allowing the doctors 7-1 to 7-n to conduct a voice communication via the communication network 4. Accordingly, the patient 6 who wants to have a conversation using the speaking unit 15 can talk with a doctor who uses the destination terminal. Thus the patient 6 can be given instructions on medication etc. The doctor can also call the center terminal 3 depending on the condition of the patient 6 to call an ambulance or, alternatively, the doctor himself can call an ambulance.

In step Sa12, the control unit 16 waits for the termination of conversation in this state. When the conversation has ended, the control unit 16 returns to the standby mode in steps Sa1 and Sa2.

When a fixed time has passed without the message button 12 depressed in the standby mode of steps Sa5 and Sa6, the control unit 16 proceeds from step Sa5 to step Sa13. In step Sa13, the control unit 16 instructs the communication unit 14 to call the center terminal 3. Then, in step Sa14, the control unit 16 waits for a response to the call. When the center terminal 3 responds to the call into connection via the communication network 4, the control unit 16 proceeds from the step Sa14 to step Sa15. In step Sa15, the control unit 16 transmits the vital data stored in the storage unit 13 in Step Sa3 to the communication network 4. Then the vital data is sent to the center terminal 3 via the communication network 4. The center terminal 3 has the function of receiving the vital data via the communication network 4 and displaying the contents of the vital data. Accordingly, the contents of the vital data are displayed on the center terminal 3, so that the person in charge 8 can check the condition of the originating patient 6. After transmitting the vital data, in step Sa16, the control unit 16 automatically terminates the conversation irrespective of the intention of the patient 6 or the person in charge 8. Then the control unit 16 returns to the standby mode of steps Sa1 and Sa2.

When the message button 12 is depressed in the standby mode of steps Sa1 and Sa2, the control unit 16 proceeds from step Sa2 to step Sa17. In step Sa17, the control unit 16 instructs the communication unit 14 to call the center terminal 3. Then, in step Sa18, the control unit 16 waits for a response to the call. When the center terminal 3 responds to the call into connection via the communication network 4, the control unit 16 proceeds from the step Sa18 to step Sa19. In step Sa19, the control unit 16 transmits the vital data stored in the storage unit 13 in Step Sa3 to the communication network 4. Thus, the contents of the vital data are displayed on the center terminal 3, so that the person in charge 8 can check the condition of the originating patient 6. The center terminal 3 has the function of allowing the person in charge 8 to conduct a voice communication via the communication network 4. Accordingly, the patient 6 who wants to have a conversation using the speaking unit 15 can talk with the person in charge 8.

In step Sa20, the control unit 16 waits for the termination of the conversation in this state. When the conversation has ended, the control unit 16 returns to the standby mode in steps Sa1 and Sa2.

As has been described above, according to the first embodiment, when the patient 6 feels bad in health and so depresses the message button 12 and also the vital data measured by the measuring device 5 mounted to the patient 6 contains an abnormal value, the patient terminal 1 is connected any of the doctor terminals 2-1 to 2-n. Accordingly, the patient 6 can directly consult the doctors 7-1 to 7-n for the condition of his/her health. According to the first embodiment, the vital data is sent to a doctor terminal connected to the patient terminal 1, where it is displayed on the doctor terminal. The doctor can therefore grasp the condition of the health of the patient 6 while viewing the vital data.

According to the first embodiment, when a selected doctor terminal does not respond to a call, the system tries calling another doctor terminal. Accordingly, when a doctor who uses the selected doctor terminal cannot respond to the call for the reason that the doctor is engaged, another free doctor can respond to it. According to the first embodiment, the doctor terminal is selected in a predetermined order. This prevents unbalance of loads on a specific doctor due to concentration of selection to the specific doctor.

According to the first embodiment, the patient terminal 1 is connected to the center terminal 3 in response to the fact that a state in which the message button 12 is not depressed is left as it is for a fixed time although the vital data indicates an abnormal value. When the vital data has been transmitted, conversation is forced to terminate from the patient terminal 1. The foregoing situation may be a case in which the patient 6 does not depress the message button 12 because of having no subjective symptom or a case in which the patient 6 cannot depress the message button 12 because of losing consciousness. The person in charge 8 of the center terminal 3 can find the foregoing situation from the above-described operation of the center terminal 3 or the abnormal vital data sent from the patient terminal 1. Thus, the person in charge 8 can check the presence or absence of the consciousness of the patient 6 by calling back the patient 6 or the like, wherein when the patient 6 is conscious, the person in charge 8 can inform the patient 6 of the abnormality of the vital data and advise him/her to consult a doctor immediately. Alternatively, the person in charge 8 can transfer the conversation with the patient terminal 1 to one of the doctor terminals 2-1 to 2-n, thereby giving advice from the doctor to the patient 6. When the patient 6 is unconscious, the person in charge 8 can call an ambulance etc. The processes by the person in charge 8, exemplified as above, are not necessarily performed by the doctors 7-1 to 7-n. In such a situation, the patient terminal 1 connects to the center terminal 3 not to the doctor terminals 2-1 to 2-n. This eliminates the need for the doctors 7-1 to 7-n to perform the foregoing processes, thus reducing loads on the doctors 7-1 to 7-n.

According to the first embodiment, a situation in which the message button 12 is depressed when the vital data contains no abnormality may be a case in which the patient 6 should be under observation because no urgent treatment is required or a case in which it is not caused by the relevant disease. The patient terminal 1 is thus connected to the center terminal 3, in which case the connection between the patient terminal 1 and the center terminal 3 is maintained also after the vital data has been sent, allowing the patient 6 to have a conversation with the person in charge 8. Accordingly, the person in charge 8 can hear the condition from the patient 6 and search for a connectable doctor to connect to the patient 6 only when necessary, while the person in charge 8 can take a necessary step without involvement by a doctor for only a question or consultation. This results in the reduction of loads on the doctors 7-1 to 7-n.

According to the first embodiment, effective home-care medical service can be provided while loads on the doctors 7-1 to 7-n are reduced.

The use of the healthcare support system according to the first embodiment allows the patient terminal 1 to serve as the contact of a hospital. In other words, time-consuming jobs such as application at the reception counter of a hospital, payment, the receipt of prescriptions, and the receipt of medicine at a pharmacy can be performed at home, thus reducing the time that outpatients must be in hospital.

This also allows patients to be given treatments such as an injection or intravenous drip injection only by visiting a pharmacy in the neighborhood according to the results of a medical examination via telemedicine if allowed legally.

Second Embodiment

Figure 5:
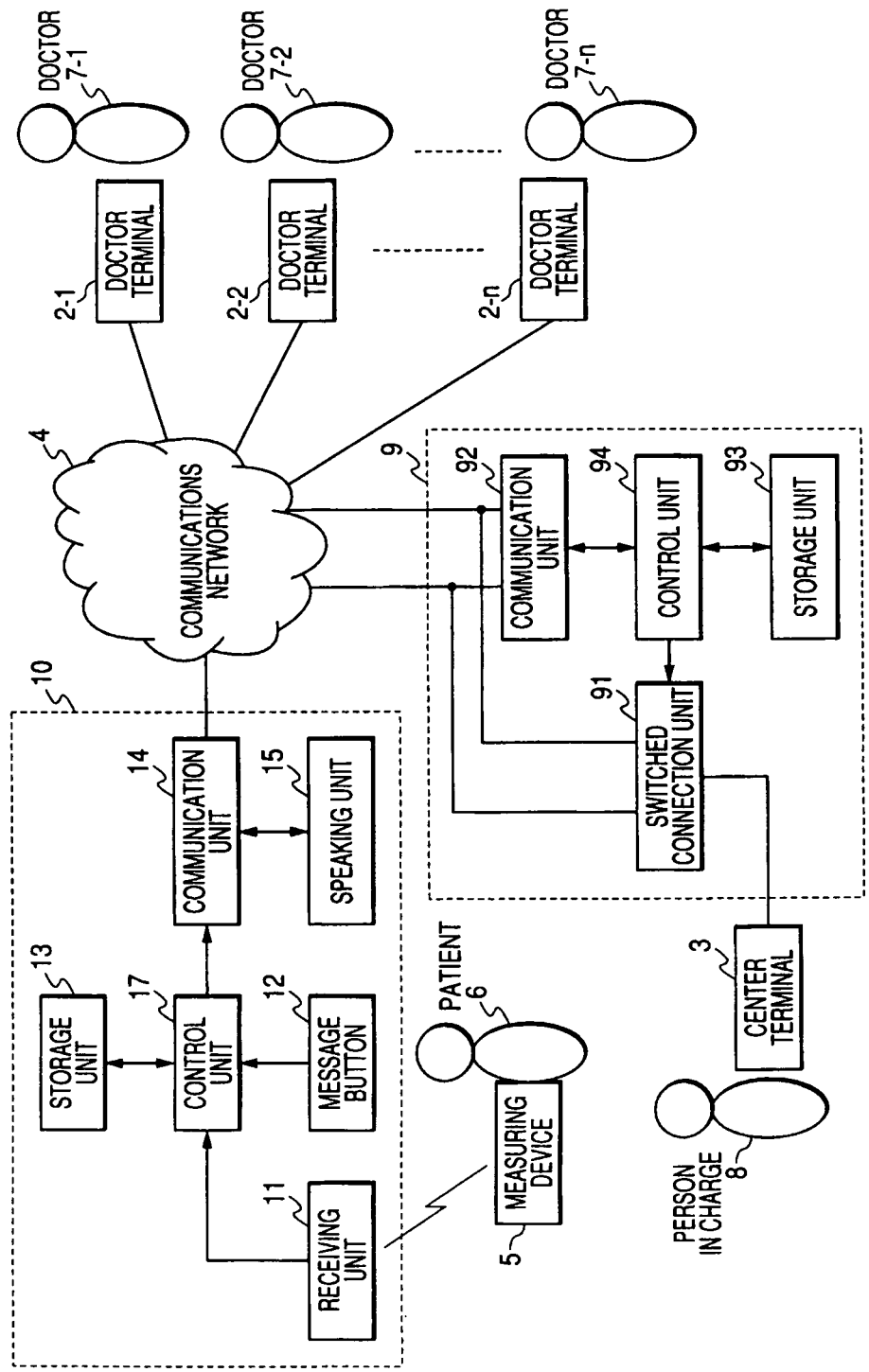
FIG. 5 is a block diagram showing the structure of a healthcare support system according to a second embodiment of the present invention.

FIG. 5 is a block diagram showing the structure of a healthcare support system according to a second embodiment of the invention. The same components as those of FIG. 1 are given the same reference numerals and their detailed description will be omitted.

As shown in FIG. 5, the healthcare support system according to the second embodiment includes the doctor terminals 2-1 to 2-n, a center terminal 9, and a patient terminal 10, each of which is connected to the communication network 4. The center terminal 3 connects to the center terminal 9. The healthcare support system provides a healthcare support service capable of responding to a message from the patient terminal 10 by using the doctor terminals 2-1 to 2-n and the center terminal 3. Accordingly, the doctor terminals 2-1 to 2-n and the center terminal 3 are terminals on the side that provides the service.

The center terminal 9 is one of the forms of the healthcare support apparatus according to the invention. The center terminal 9 includes a switched connection unit 91, a communication unit 92, a storage unit 93, and a control unit 94.

The center terminal 9 connects to the communication network 4 via multiple communication channels. The switched connection unit 91 freely switches the connection between the multiple communication channels and the center terminal 3.

The communication unit 92 performs communication processing for achieving communication via the communication network 4.

The storage unit 93 temporarily stores various information including vital data. The storage unit 93 stores information necessary to send a message to medical institutions. The storage unit 93 also stores information similar to the call information and order information stored in the storage unit 13 in the first embodiment.

The control unit 94 is constructed so that, for example, a CPU executes an application program. The control unit 94 performs the later-described processing for allowing the center terminal 9 to mediate a message.

The patient terminal 10 includes the receiving unit 11, the message button 12, the storage unit 13, the communication unit 14, the speaking unit 15, and a control unit 17. In other words, the patient terminal 10 includes the control unit 17 in place of the control unit 16 of the patient terminal 1 in the first embodiment.

The control unit 17 is achieved by, for example, the CPU executing the application program. The control unit 17 performs the later-described processing for allowing the patient terminal 10 to send a message.

The storage unit 13 stores call information for calling the center terminal 9 but does not store the call information and order information stored in the storage unit 13 in the first embodiment.

Figure 6:
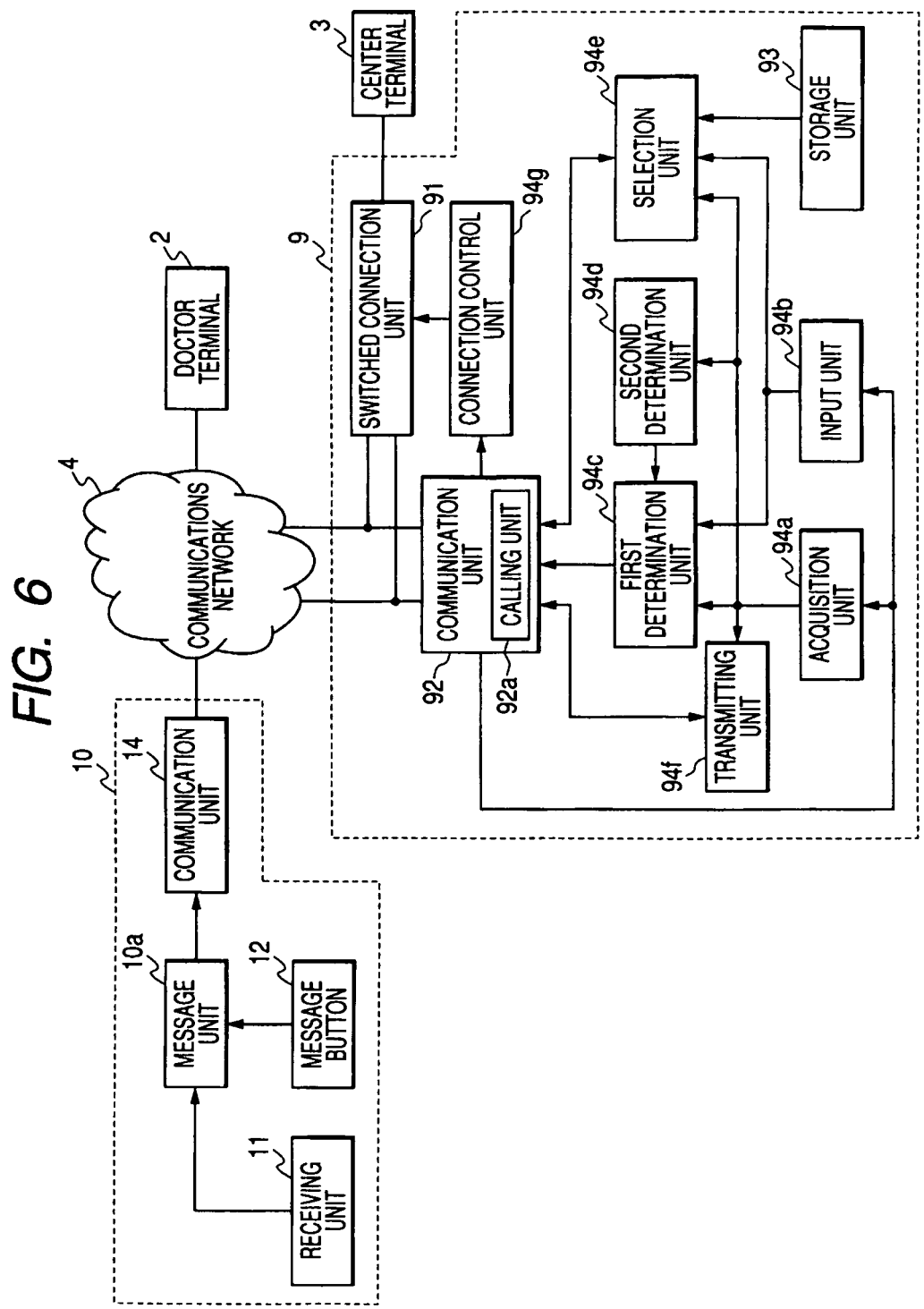
FIG. 6 is a block diagram showing the function of the patient terminal and the center apparatus in FIG. 5.

FIG. 6 is a block diagram showing the function of the center terminal 9 and the patient terminal 10 in FIG. 5. The same components as those of FIG. 6 are given the same reference numerals and their detailed description will be omitted.

A message unit 10*a* shown in FIG. 6 serves as one of the functions of the control unit 17.

The message unit 10*a* determines the necessity of messaging according to vital data outputted from the receiving unit 11 and the output state of the depression signal from and the message button 12. When the message unit 10*a* determines that a message should be given, it transmits the vital data and message information including intention-absence information or intention-presence information, to be described later, to the center terminal 9.

An acquisition unit 94*a*, an input unit 94*b*, a first determination unit 94*c*, a second determination unit 94*d*, a selection unit 94*e*, a transmitting unit 94*f*, and a connection control unit 94*g* of FIG. 6 are each achieved as one of the functions of a control unit 94.

Message information sent from the patient terminal 10 is received by the communication unit 92 and inputted to the acquisition unit 94*a* and the input unit 94*b*. The acquisition unit 94*a* acquires vital data from the message information. The input unit 94*b* extracts intention-absence information or intension-presence information from the message information and thereby inputs the presence or absence of messaging request.

The second determination unit 94*d* determines whether or not the vital data outputted from the acquisition unit 94*a* contains an abnormal value. The first determination unit 94*c* determines the necessity of messaging according to the vital data outputted from the acquisition unit 94*a*, the presence or absence of messaging request inputted from the input unit 94*b*, and the determination of the second determination unit 94*d*. The selection unit 94*e* selects a destination terminal according to the vital data outputted from the acquisition unit 94*a*, the presence or absence of messaging request inputted from the input unit 94*b*, and the order information stored in the storage unit 93. The transmitting unit 94*f* transmits the vital data outputted from the acquisition unit 94*a* to the destination terminal. The connection control unit 94*g* controls the switched connection unit 91 so as to connect the doctor terminals 2, the center terminal 3, and the patient terminal 10 appropriately.

The communication unit 92 includes a calling unit 92*a*. The calling unit 92*a* calls the destination terminal selected by the selection unit 94*e*.

The operation of the healthcare support system with such a structure will now be described.

Figure 7:
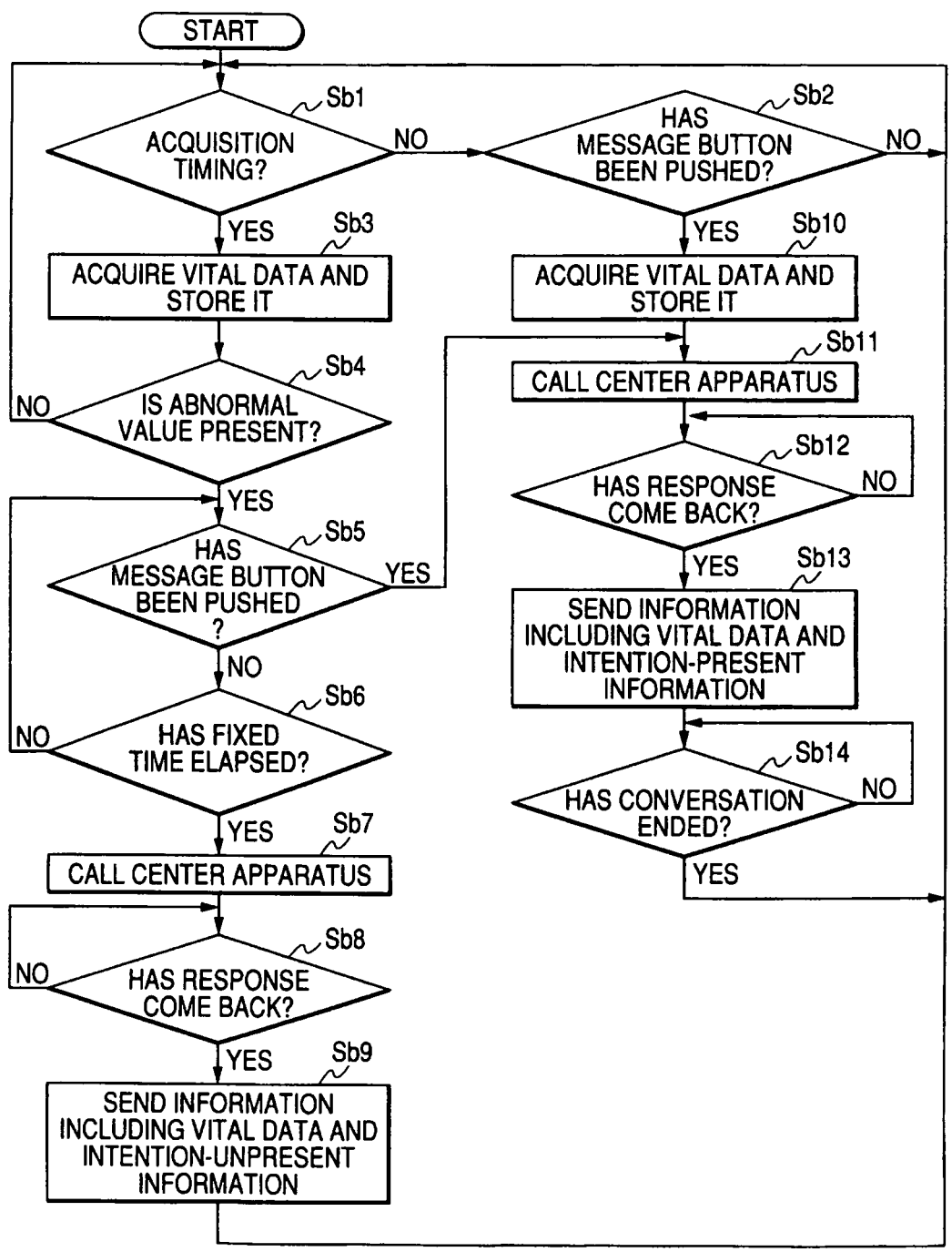
FIG. 7 is a flowchart for a procedure of the control unit in FIG. 5.

Upon activation of the patient terminal 10, the control unit 17 starts the processing shown in FIG. 7.

In steps Sb1 and Sb2, the control unit 17 waits for an acquisition timing or the depression of the message button 12.

When the acquisition timing has come, the control unit 17 proceeds from step Sb1 to step Sb3. In step Sb3, the control unit 17 acquires vital data received by the receiving unit 11 and stores the vital data in the storage unit 13. Subsequently, in step Sb4, the control unit 17 determines whether or not the acquired vital data contains an abnormal value. When no abnormal value is contained, the control unit 17 returns from step Sb4 to the standby mode in steps Sb1 and Sb2.

In contrast, when the vital data contains an abnormal value, the control unit 17 proceeds from step Sb4 to the standby mode in steps Sb5 and Sb6. In the standby mode of steps Sb5 and Sb6, the control unit 17 waits for a lapse of a fixed time after entry to the standby mode or the depression of the message button 12.

When a fixed time has passed without the message button 12 depressed, the control unit 17 proceeds from step Sb6 to step Sb7. In step Sb7, the control unit 17 instructs the communication unit 14 to call the center terminal 9. Then, in step Sb8, the control unit 17 waits for a response to the call. When the center terminal 9 responds to the call into connection via the communication network 4, the control unit 17 proceeds from step Sb8 to step Sb9. In step Sb9, the control unit 17 transmits message information to the communication network 4. The message information to be transmitted here contains the vital data stored in the storage unit 13 in step Sb3 and intention-absence information. The intention-absence information indicates that the message button 12 has not been depressed, or the patient 6 has no intention of giving a message. After completion of the transmission of the message information, the control unit 17 returns to the standby mode of steps Sb1 and Sb2. The message information transmitted from the patient terminal 10 is sent to the center terminal 9 via the communication network 4.

When the message button 12 is depressed in the standby mode of steps Sb1 and Sb2, the control unit 17 proceeds from step Sb2 to step Sb10. In step Sb10, the control unit 17 acquires vital data received by the receiving unit 11 and stores the vital data in the storage unit 13. The control unit 17 thereafter proceeds to step Sb11.

On the other hand, when the message button 12 is depressed before a lapse of a fixed time in the standby mode of steps Sb5 and Sb6, the control unit 17 proceeds to step Sb11.

In step Sb11, the control unit 17 instructs the communication unit 14 to call the center terminal 9. Then, in step Sb12, the control unit 17 waits for a response to the call. When the center terminal 9 responds to the call into connection via the communication network 4, the control unit 17 proceeds from the step Sb12 to step Sb13. In step Sb13, the control unit 17 transmits message information to the communication network 4. The message information to be transmitted here contains the vital data stored in the storage unit 13 in step Sb3 and intention-presence information. The intention-presence information indicates that the message button 12 has been depressed, or the patient 6 has the intention of giving a message. After completion of the transmission of the message information, the control unit 17 proceeds to step Sb14. In step Sb14, the control unit 17 waits for the termination of conversation, in which case the connection of the patient terminal 10 with the center terminal 9 is maintained. After conversation has ended, the control unit 17 returns to the standby mode of steps Sb1 and Sb2.

Figure 8:
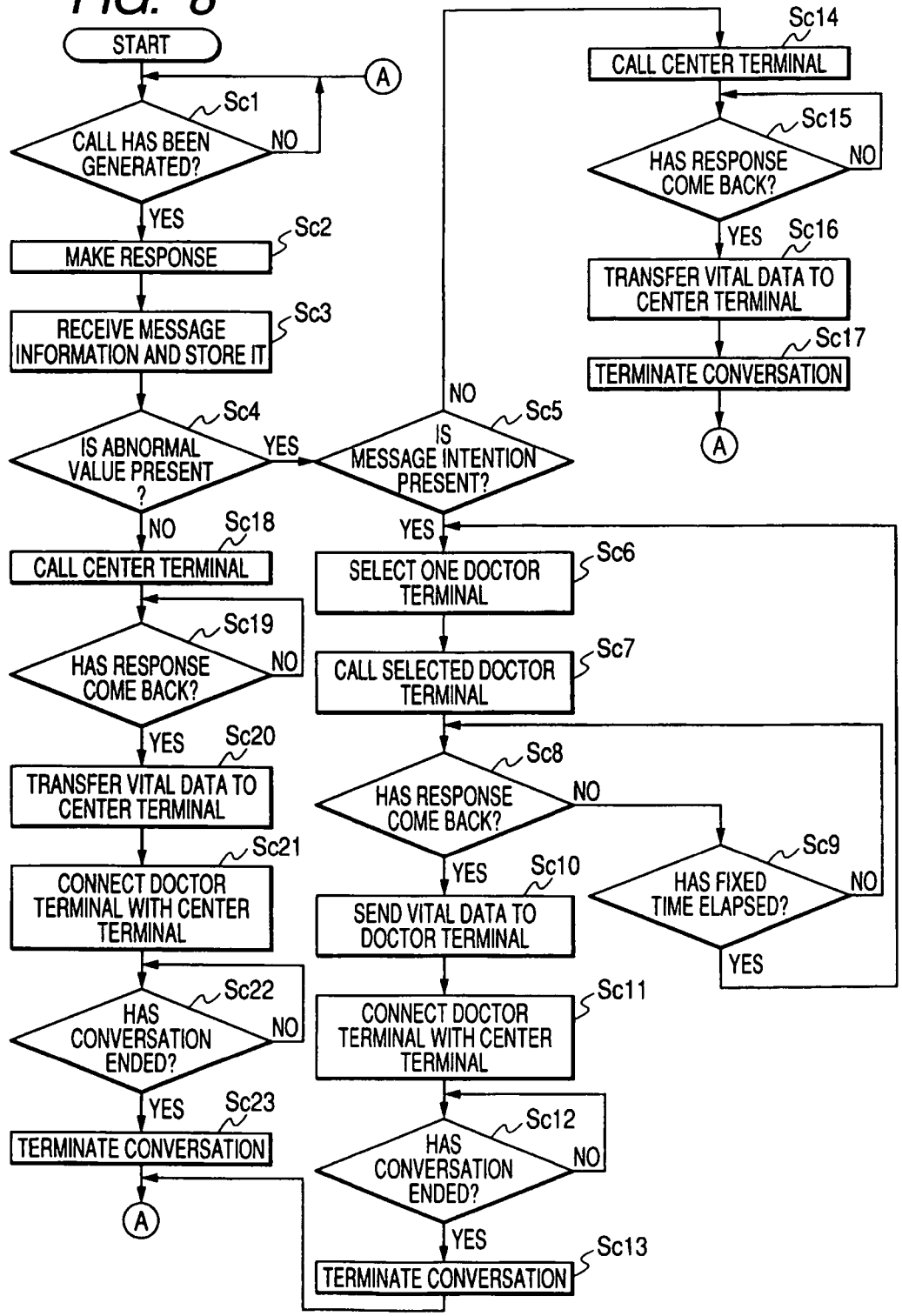
FIG. 8 is a flowchart for a procedure of the control unit in FIG. 5.

Upon activation of the center terminal 9, the control unit 94 starts the processing shown in FIG. 8.

In step Sc1, the control unit 94 waits for calling from the patient terminal 10. When the patient terminal 10 originates a call, as described above, the control unit 94 proceeds from step Sc1 to step Sc2. In step Sc2, the control unit 94 makes the communication unit 92 perform processing of responding to the call. The center terminal 9 is thus connected to the patient terminal 10 via the communication network 4. Then the message information transmitted from the patient terminal 10 comes via the communication network 4. In step Sc3, the control unit 94 instructs the communication unit 92 to receive the message information and stores the message information received by the communication unit 92 into the storage unit 93.

Subsequently, in step Sc4, the control unit 94 determines whether or not the vital data in the message information contains an abnormal value, wherein when an abnormal value is contained, the control unit 94 proceeds from step Sc4 to step Sc5. In step Sc5, the control unit 94 checks which of intention-presence information and intention-absence information is contained in the message information, thereby determining whether the patient 6 has the intention of giving a message.

When it is determined that the patient 6 has the intention of giving a message, the control unit 94 proceeds from step Sc5 to step Sc6. In step Sc6, the control unit 94 selects one of the doctor terminals 2-1 to 2-$n$ according to the order information stored in the storage unit 13. When all doctor terminals in the same group have been selected and a doctor terminal to be selected next is designated by group, the control unit 94 selects one of the doctor terminals in the designated group as a destination terminal in accordance with a predetermined condition (e.g., at random). In step Sc7, the control unit 94 instructs the communication unit 14 to call the foregoing selected destination terminal. The control unit 94 then moves to a standby mode in steps Sc8 and Sc9. In steps Sc8 and Sc9, the control unit 94 waits for a response to the call or a lapse of a fixed time after entering the standby mode.

When no response is given within a fixed time, the control unit 94 returns from step Sc9 to step Sc6, wherein the control unit 94 selects another doctor terminal as a destination terminal and tries calling. When the destination terminal responds to the call into connection via the communication network 4, the control unit 94 proceeds from step Sc8 to step Sc10. In step Sc10, the control unit 94 transmits the vital data stored in the storage unit 13 in step Sc3 to the destination terminal. In step Sc11, the control unit 94 then instructs the switched connection unit 91 to connect the patient terminal 1 with the destination terminal. The doctor terminals 2-1 to 2-$n$ have the function of receiving vital data via the communication network 4 and displaying the contents of the vital data. Accordingly, the contents of the vital data are displayed on the destination terminal, so that a doctor who uses the destination terminal can check the condition of the originating patient 6. The doctor terminals 2-1 to 2-$n$ also have the function of allowing the doctors 7-1 to 7-$n$ to conduct a voice communication via the communication network 4. Accordingly, the patient 6 who wants to have a conversation using the speaking unit 15 can talk with a doctor who uses the destination terminal. Thus the patient 6 is given instructions on medication etc. The doctor can also call the center terminal 3 depending on the condition of the patient 6 to call an ambulance or, alternatively, the doctor himself can call an ambulance.

In step Sa12, the control unit 94 waits for the termination of conversation from one of the patient terminal 1 and the destination terminal in this state. When the conversation has ended, the control unit 94 proceeds from step Sc12 to step Sc13. In step Sc13, the control unit 94 terminates conversation. In the termination of conversation, the control unit 94 instructs the switched connection unit 91 to release, for example, the connection between the patient terminal 1 and the destination terminal and instructs the communication unit 92 to terminate conversation for a terminal that has not terminated conversation. Then, the control unit 94 returns to the standby mode of step Sc1.

When it is determined in step Sc5 that the patient 6 has the intention of giving a message, the control unit 94 proceeds from step Sc5 to step Sc14. In step Sc14, the control unit 94 instructs the communication unit 92 to call the center terminal 3. Then, in step Sc15, the control unit 94 waits for a response to the call. When the center terminal 3 responds to the call, the control unit 94 proceeds from the step Sc15 to step Sc16. In step Sc16, the control unit 94 transfers the vital data stored in the storage unit 13 in Step Sc3 to the center terminal 3. The center terminal 3 has the function of receiving vital data and displaying the contents of the vital data. Accordingly, the contents of the vital data are displayed on the center terminal 3, so that the person in charge 8 can check the condition of the originating patient 6. After transmitting the vital data, in step Sc17, the control unit 94 automatically terminates the conversation irrespective of the intention of the patient 6 or the person in charge 8. Then the control unit 94 returns to the standby mode of step Sc1.

When the vital data contained in the message information has no abnormal value, the control unit 94 proceeds from step Sc4 to step Sc18. In step Sc18, the control unit 94 calls the center terminal 3. Then, in step Sc19, the control unit 94 waits for a response to the call. When the center terminal 3 responds to the call, the control unit 94 proceeds from step Sc19 to step Sc20. In step Sc20, the control unit 94 transfers the vital data stored in the storage unit 13 in Step Sc3 to the center terminal 3. In step Sc21, the control unit 94 then instructs the switched connection unit 91 to connect the patient terminal 1 with the center terminal 3. Accordingly, the contents of the vital data are displayed on the center terminal 3, so that the person in charge 8 can check the condition of the originating patient 6. The center terminal 3 has the function of allowing the person in charge 8 to conduct a voice communication via the communication network 4. Accordingly, the patient 6 who wants to have a conversation using the speaking unit 15 can talk with the person in charge 8.

In step Sc22, the control unit 94 waits for the termination of the conversation by one of the patient terminal 1 and the center terminal 3 in this state. When the conversation has ended, the control unit 94 proceeds from step Sc22 to Sc23. In step Sc23, the control unit 94 terminates conversation. In the termination of conversation, the control unit 94 instructs the switched connection unit 91 to release the connection, for example, between the patient terminal 1 and the center terminal 3 and terminates conversation for a terminal that has not terminated conversation. Then, the control unit 94 returns to the standby mode of step Sc1.

As has been described, according to the second embodiment, effective home-care medical service can be provided while loads on the doctors 7-1 to 7-$n$ are reduced, as in the first embodiment.

According to the second embodiment, the patient terminal 10 always calls the center terminal 9, not selecting the destination terminal. Accordingly, the patient terminal 10 can be achieved with a simple structure as compared with the patient terminal 1. When there are multiple patients 6, multiple patient terminals 10 are required. Therefore, the simple structure of the patient terminal 10 greatly reduces the cost for constructing the healthcare support system. Also when the necessity for changing the selecting order arises, it can be addressed by merely changing the setting of the center terminal 9. In short, the flexibility of systems operation can be increased.

Third Embodiment

Figure 9:
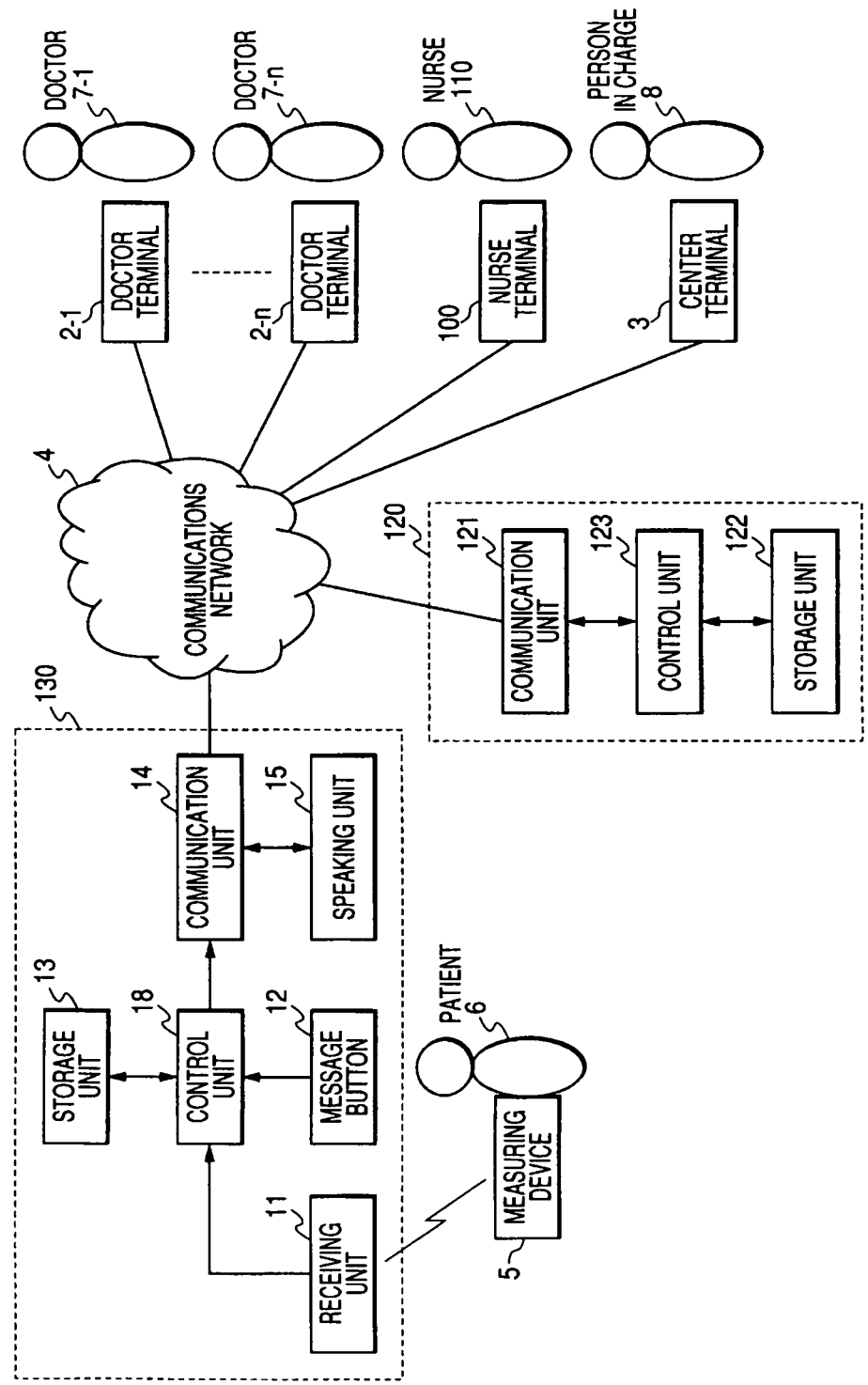
FIG. 9 is a block diagram showing the structure of a healthcare support system according to a third embodiment of the present invention.

FIG. 9 is a block diagram showing the structure of a healthcare support system according to a third embodiment of the present invention. The same components as those of FIG. 1 are given the same reference numerals and their detailed description will be omitted.

As shown in FIG. 9, the healthcare support system according to the third embodiment includes the doctor terminals 2-1 to 2-n, the center terminal 3, a nurse terminal 100, a healthcare support apparatus 120, and a patient terminal 130, each of which is connected to the communication network 4. The healthcare support system provides a healthcare support service capable of responding to a message from the patient terminal 130 by using the doctor terminals 2-1 to 2-n, the center terminal 3, and the nurse terminal 100. Accordingly, the doctor terminals 2-1 to 2-n, the center terminal 3, and the nurse terminal 100 are terminals on the side that provides the service.

The healthcare support apparatus 120 includes a communication unit 121, a storage unit 122, and a control unit 123.

The communication unit 121 performs communication processing for achieving communication via the communication network 4.

The storage unit 122 temporarily stores various information including vital data. The storage unit 122 stores information necessary to send a message to medical institutions. The storage unit 122 also stores information on the patient 6 and destination-terminal selecting conditions for each patient 6. The patient information includes the names of patients, call information (e.g., telephone numbers) for calling the patient terminal 130, etc.

The control unit 123 is achieved by, for example, a CPU executing an application program. The control unit 123 performs the later-described processing for allowing the healthcare support apparatus 120 to mediate a message.

The patient terminal 130 includes the receiving unit 11, the message button 12, the storage unit 13, the communication unit 14, the speaking unit 15, and a control unit 18. In other words, the patient terminal 130 includes the control unit 18 in place of the control unit 16 of the patient terminal 1 in the first embodiment.

The control unit 18 is achieved by, for example, the CPU executing the application program. The control unit 18 performs the later-described processing for allowing the patient terminal 130 to send a message.

The storage unit 13 stores call information for calling the healthcare support apparatus 120 but does not store the call information and order information stored in the storage unit 13 in the first embodiment.

Figure 10:
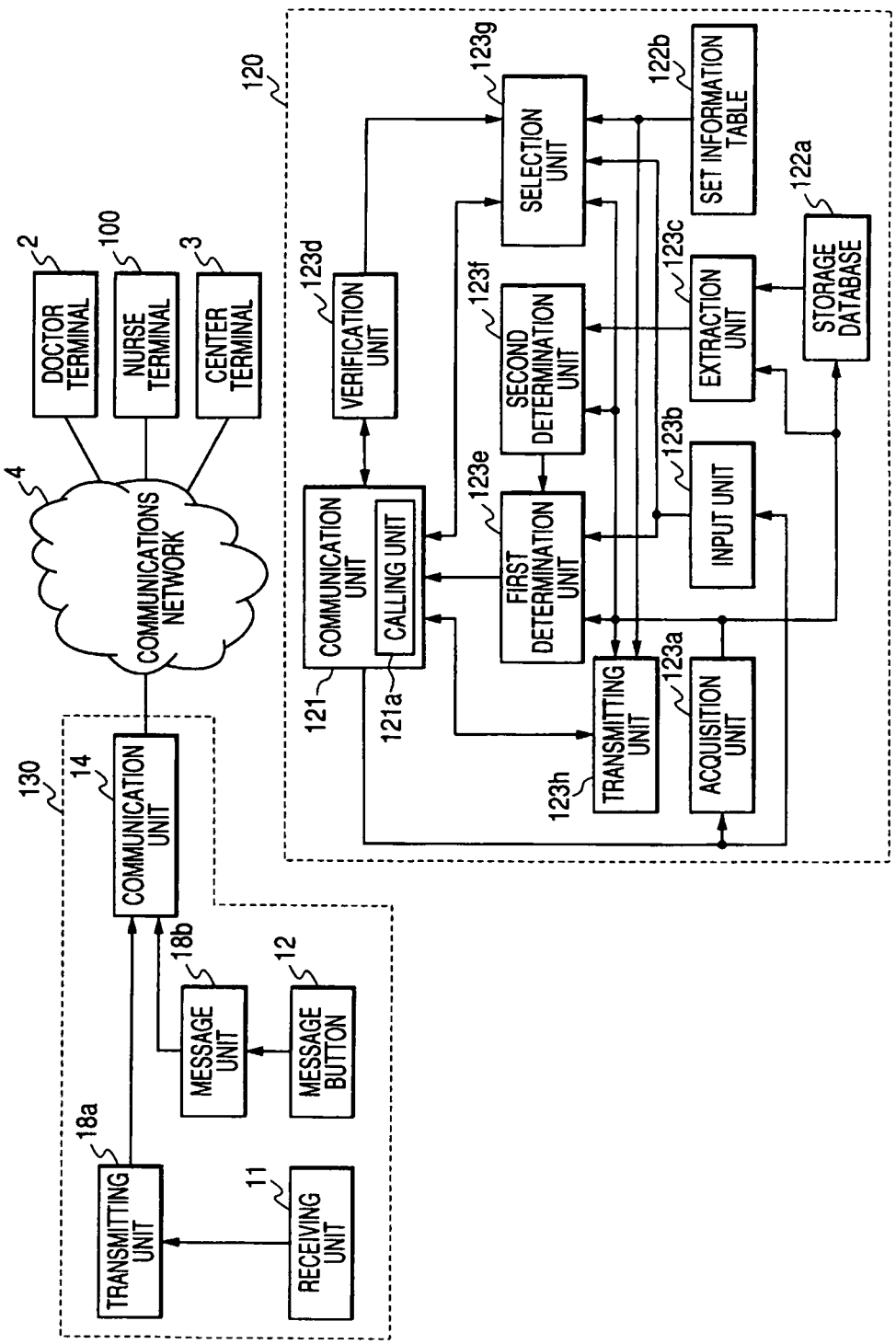
FIG. 10 is a block diagram showing the function of the patient terminal and the healthcare support apparatus in FIG. 9.

FIG. 10 is a block diagram showing the function of the healthcare support apparatus 120 and the patient terminal 130 in FIG. 9. The same components as those of FIG. 9 are given the same reference numerals and their detailed description will be omitted.

A transmitting unit 18a and a message unit 18b in FIG. 10 are each achieved as one of the functions of the control unit 18.

The transmitting unit 18a regularly transmits vital data outputted from the receiving unit 11 to the healthcare support apparatus 120. The message unit 18b informs the healthcare support apparatus 120 of the fact that a messaging request is given in response to the output of a depression signal from the message button 12.

A storage database 122a and a set information table 122b shown in FIG. 10 are provided in part of the storage region of the storage unit 122. An acquisition unit 123a, an input unit 123b, an extraction unit 123c, a verification unit 123d, a first determination unit 123e, a second determination unit 123f, a selection unit 123g, and a transmitting unit 123h of FIG. 10 serve as the function of the control unit 123.

The set information table 122b lists the above-described patient information and selecting conditions.

Information sent from the patient terminal 130 is received by the communication unit 121 and then inputted to the acquisition unit 123a and the input unit 123b. The acquisition unit 123a acquires vital data from the foregoing information. The vital data acquired by the acquisition unit 123a is stored in the storage database 122a. The storage database 122a stores vital data acquired in the past. The input unit 123b inputs a messaging request by extracting a notification that a messaging request is given from the foregoing information.

When the acquisition unit 123a acquires new vital data of the patient 6, the extraction unit 123c extracts past vital data of the patient 6 related to the new vital data from the storage database 122a. The verification unit 123d verifies the respective conditions of the doctor terminals 2-1 to 2-n via the communication unit 121 and the communication network 4 and determines whether or not to allow a message.

The second determination unit 123f determines whether or not the vital data outputted from the acquisition unit 123a contains an abnormal value with reference to the vital data extracted by the extraction unit 123c. The first determination unit 123e determines the necessity of messaging from the vital data outputted from the acquisition unit 123a, the presence or absence of a messaging request inputted from the input unit 123b, and the determination of the second determination unit 123f. The selection unit 123g selects a destination terminal according to the vital data outputted from the acquisition unit 123a, the presence or absence of the messaging request inputted from the input unit 123b, and the set information stored in the set information table 122b.

The transmitting unit 123h transmits the vital data outputted from the acquisition unit 123a to a destination terminal. The transmitting unit 123h also reads information on the patient related to the vital data from the set information table and sends the patient information to the destination terminal.

The communication unit 121 includes a calling unit 121a. The calling unit 121a calls the destination terminal selected by the selection unit 123g.

Then the operation of the healthcare support system with such a structure will be described.

Figure 11:
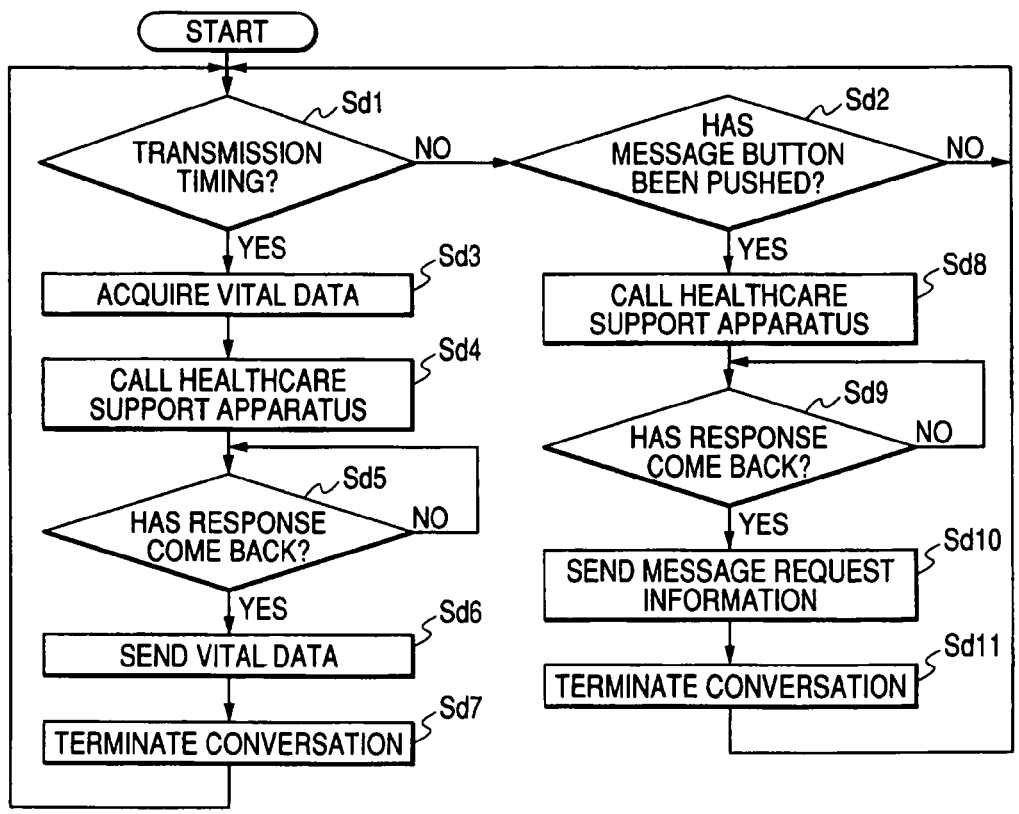
FIG. 11 is a flowchart for a procedure of the control unit in FIG. 9.

Upon activation of the patient terminal 130, the control unit 18 starts the processing shown in FIG. 11.

In steps Sd1 and Sd2, the control unit 18 waits for a timing to transmit vital data to the healthcare support apparatus 120 (hereinafter, referred to as a transmission timing) or the depression of the message button 12. The transmission timing may be determined freely or, for example, at a predetermined time or at regular intervals.

When the transmission timing has come, the control unit 18 proceeds from step Sd1 to step Sd3. In step Sd3, the control unit 18 acquires vital data received by the receiving unit 11. Subsequently, in step Sd4, the control unit 18 instructs the communication unit 14 to call the healthcare support apparatus 120. Thereafter, in step Sd5, the control unit 18 waits for a response to the call. When the healthcare support apparatus 120 makes a response into connection via the communication network 4, the control unit 18 proceeds from the step Sd5 to step Sd6. In step Sd6, the control unit 18 transmits the vital data acquired in step Sd3 to the healthcare support apparatus 120. After completion of transmission of the vital data, the control unit 18 proceeds from step Sd6 to step Sd7. In step Sd7, the control unit 18 performs a conversation terminating process for releasing the connection with the healthcare support apparatus 120. Then the control unit 18 returns to the standby mode in steps Sd1 and Sd2.

When the message button 12 is depressed in the standby mode of steps Sd1 and Sd2, the control unit 18 proceeds from step Sd2 to step Sd8. In step Sd8, the control unit 18 instructs the communication unit 14 to call the healthcare support apparatus 120. Then, in step Sd9, the control unit 18 waits for a response to the call. When the healthcare support apparatus 120 responds to the call into connection via the communication network 4, the control unit 18 proceeds from the step Sd9 to step Sd10. In step Sd10, the control unit 18 transmits message information, indicative of the fact that a messaging request is given from the patient 6, to the healthcare support apparatus 120. After completion of transmission of the message information, the control unit 18 proceeds from step Sd10 to step Sd11. In step Sd11, the control unit 18 performs a conversation terminating process for releasing the connection with the healthcare support apparatus 120. Then the control unit 18 returns to the standby mode in steps Sd1 and Sd2.

As has been described above, the patient terminal 130 transmits healthcare date regularly and message information in response to a messaging request but does not perform determination of the necessity of messaging and selection of a destination terminal. The healthcare support apparatus 120 and the patient terminal 130 may be connected together via an exclusive line so that healthcare data can be transmitted continually from the patient terminal 130 to the healthcare support apparatus 120.

Figure 12:
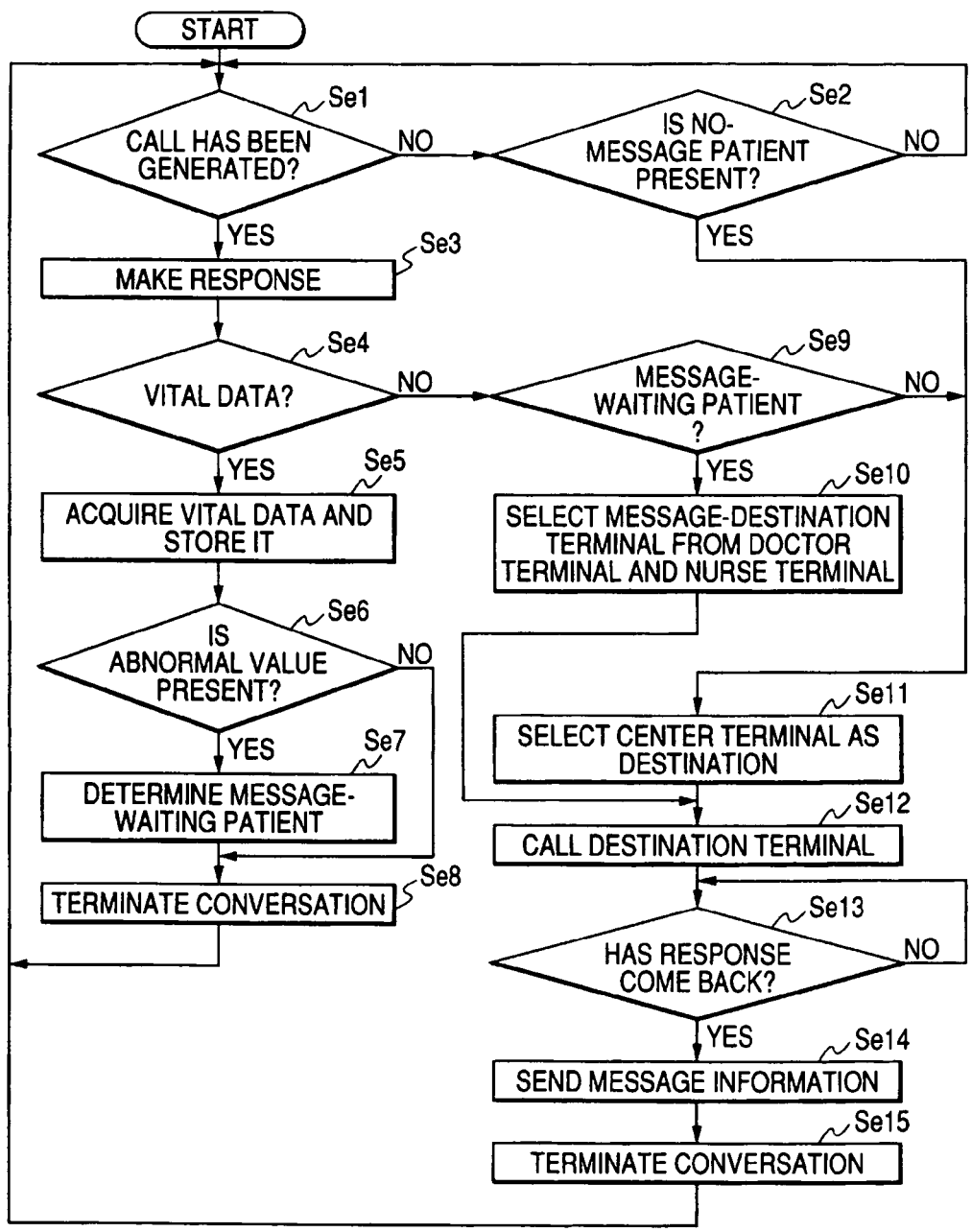
FIG. 12 is a flowchart for a procedure of the control unit in FIG. 9.

Upon activation of the healthcare support apparatus 120, the control unit 123 starts the processing shown in FIG. 12.

In steps Se1 and Se2, the control unit 123 waits for a call from the patient terminal 130 or the generation of a no-message patient. When a call is originated from the patient terminal 130, the control unit 123 proceeds from step Se1 to step Se3. In step Se3, the control unit 123 makes the communication unit 121 respond to the call. Thus the healthcare support apparatus 120 is connected to the patient terminal 130 via the communication network 4. Thus the healthcare data or message information transmitted from the patient terminal 130 comes via the communication network 4, as described above. The healthcare data or message information is received by the communication unit 121.

In step Se4, the control unit 123 determines which of the healthcare data and the message information the communication unit 121 has received. When the communication unit 121 has received the healthcare data, the control unit 123 shifts from step Se4 to step Se5. In step Se5, the control unit 123 acquires the vital data received by the communication unit 121 and stores it in the storage unit 122. The storage unit 122 stores vital data on the same patient 6 in time sequence.

In step Se6, the control unit 123 checks whether or not the acquired vital data contains an abnormal value. The control unit 123 determines that an abnormal value is contained when the trend of the vital data changes rapidly. More specifically, the control unit 123 first calculates the reference value of the vital data from the patient's vital data stored in the storage unit 122 in time sequence. Namely, available reference values include a mean value, a time integral, and a vector value. The control unit 123 compares the reference value with the value of newly acquired vital data, wherein when the difference is more than a fixed value or a fixed ratio, the control unit 123 determines that an abnormal value is contained. It is also possible to use a reference value predetermined from vital data that is acquired in advance in medical institutions.

When it is determined that an abnormal value is contained, the control unit 123 proceeds from step Se6 to step Se7. In step Se7, the control unit 123 determines a patient related to the vital data acquired in step Se5 to be a message-waiting patient. The control unit 123 then proceeds to step Se8. In contrast, when the control unit 123 determines that no abnormal value is contained, the control unit 123 passes step Se7 and proceeds from step Se6 to step Se8. In step Se8, the control unit 123 performs a conversation-terminating process for releasing the connection with the patient terminal 130. Thereafter the control unit 123 returns to the standby mode in steps Se1 and Se2.

When the communication unit 121 has received message information, the control unit 123 proceeds from step Se4 to step Se9. In step Se9, the control unit 123 checks whether or not the patient who has made the messaging request shown in the message information is determined to be a message-waiting patient. When it is determined to be a message-waiting patient, the control unit 123 proceeds from step Se9 to step Se10. In step Se10, the control unit 123 selects a destination terminal from the doctor terminal 2 and the nurse terminal 100. At that time, the control unit 123 selects the destination terminal according to the vital data on a patient who has made a messaging request and the set information stored in the storage unit 122. More specifically, the control unit 123 compares the set value shown in the set information with the latest vital data to determine the level of the messaging. For example, the control unit 123 calculates the deviation of the vital data from the set value. For example, the control unit 123 determines the level as "level A" when the deviation is from 10 percent to 30 percent, while it determines as "level B" when the deviation is 30 percent or more. When the message level is at level A, the doctor terminal 2 of a doctor in charge is selected as a destination terminal, while when the message level is at level B, the doctor terminal 2 of an attending physician is selected as a destination terminal.

The control unit 123 determines by another process whether or not the individual doctor terminals 2-1 to 2-*n* allow messaging. When the doctor terminal 2 to be selected as the destination terminal rejects the message, the control unit 123 selects another doctor terminal as a destination terminal.

Although the set value, the message level, and the correlation between the message level and the destination terminal may be common to the multiple patients 6, it is desirable to set them for each of the patients 6. Desirably, the doctor terminals 2 that a doctor in charge and an attending physician use are stored for each patient in the set information. In place of the set value, the reference value calculated in step Se6 may be used. After selecting the destination terminal in this way, the control unit 123 proceeds to step Se12.

Conversely, when a patient who has made a messaging request is not determined as a message-waiting patient, the control unit 123 proceeds from step Se9 to step Se11. Aside from this, when a patient who is determined as a message-waiting patient makes no messaging request within a fixed time after the determination of the message-waiting patient (e.g., five minutes), the control unit 123 determines that there is a no-message patient. In that case, the control unit 123 proceeds from step Se2 to step Se11. In step Se11, the control unit 123 selects the center terminal 3 or the nurse terminal 100 as a destination terminal. Thereafter the control unit 123 proceeds to step Se12.

In step Se12, the control unit 123 instructs the communication unit 121 to call the destination terminal. Then, in step Se13, the control unit 123 waits for the response of the destination terminal. When the destination terminal responds to the call into connection with the healthcare support apparatus 120 via the communication network 4, the control unit 123 proceeds from step Se13 to step Se14. In step Se14, the control unit 123 transmits message information to the destination terminal. The message information includes information on a patient who has made a messaging request or a no-message patient and the vital data of the patient.

After completion of the transmission of the message information, the control unit 123 proceeds from step Se14 to step Se15. In step Se15, the control unit 123 performs a conversation-terminating process for releasing the connection with the destination terminal. Then the control unit 123 returns to the standby mode in steps Se1 to step Se2.

The doctor terminals 2-1 to 2-n, the center terminal 3, and the nurse terminal 100 have the function of receiving message information via the communication network 4 and displaying the contents of patient information and vital data in the message information. Therefore, the contents of the patient information and vital data are displayed on the destination terminal, so that the doctor 7, the person in charge 8, and a nurse 110 can check the condition of the originating patient 6.

When the vital data contains an abnormal value and the patient 6 makes a messaging request, the doctor terminal 2 is selected as a destination terminal by the operation of the healthcare support apparatus 120. In other words, when the vital data contains an abnormal value and the patient 6 has a subjective symptom, a message thereof is sent to the doctor 7. The doctor 7 who has received the message contacts the patient 6 according to the patient information displayed on the terminal, thus checking the symptom or giving instructions on medication etc. The doctor 7 can also call the center terminal 3 depending on the condition of the patient 6 to call an ambulance or, alternatively, the doctor 7 himself can call an ambulance.

On the other hand, when the patient 6 has made a messaging request although the vital data contains no abnormal value, or when the patient 6 has made no messaging request within a fixed time after abnormality has been detected in the vital data, the center terminal 3 or the nurse terminal 100 is selected as a destination terminal. In other words, when the patient 6 who has no abnormalities makes a messaging request, when the patient 6 does not depress the message button 12 because of having no subjective symptom, or when the patient 6 cannot depress the message button 12 because of losing consciousness etc., a message is first sent to an assistant other than the doctor 7, such as the person in charge 8 or the nurse 110. The person in charge 8 or the nurse 110 who received the message contacts the patient 6 according to the patient information displayed on the terminal, thus checking the presence or absence of the consciousness of the patient 6, wherein when the patient 6 is conscious, the person in charge 8 or the nurse 110 informs the patient 6 of the abnormality of the vital data and giving an advice to contact a doctor immediately. When the patient 6 is unconscious, the person in charge 8 or the nurse 110 can perform relief activities of calling an ambulance etc.

As has been described, according to the third embodiment, effective home-care medical service can be provided while loads on the doctors 7-1 to 7-n are reduced, as in the first and second embodiments.

According to the third embodiment, the patient terminal 130 only transmits vital data or message information, not performing determination of the necessity of messaging and selection of the destination terminal. Accordingly, the patient terminal 130 can be achieved with a simple structure as compared with the patient terminals 1 and 10. When there are multiple patients 6, multiple patient terminals 130 are required. Therefore, the simple structure of the patient terminal 130 greatly reduces the cost for constructing the healthcare support system. Also when the necessity for changing the selecting conditions arises, it can be addressed by merely changing the setting of the healthcare support apparatus 120. In short, the flexibility of systems operation can be increased.

The foregoing embodiments can be modified as follows:
The message button 12 may not provided to the patient terminals 1 and 10, but may be a separate movable thing such as a pendant so that the patient 6 can wear it.

The order of selecting one of the doctor terminals 2-1 to 2-n may be determined appropriately in consideration of information on the doctors 7-1 to 7-n, such as the number or time of works of the doctors 7-1 to 7-n, information on for which of the patients 6 the doctors 7-1 to 7-n work, or information on the patient 6 such as symptoms and complications. However, this requires the function of preparing history information for acquiring the foregoing information to be considered.

It is also preferable that the patient 6 select the destination terminal from the doctor terminals 2-1 to 2-n and the center terminal 3, wherein when the patient 6 selects the center terminal 3, the service charge for the center terminal 3 billed for the patient 6 be inexpensive as compared with that for the doctor terminals 2-1 to 2-n. This provides a choice to the patient 6 while preventing easygoing selection of the doctor terminals 2-1 to 2-n.

It is also preferable that, when the doctor terminals 2-1 to 2-n are selected as the destination, the patient 6 select one of the doctor terminals 2-1 to 2-n, and the service charge billed for the patient 6 be varied depending on the selected doctor terminal. This provides a choice to the patient 6 while preventing concentration of messages to a specific doctor.

It is also preferable to have the function of calculating the service charge billed for a patient and a fee for a doctor (principally a part based on usage under contract) from history data on patient terminals and history data on doctor terminals at the end of the month or on clearance date. At that time, it is preferable that the history data be prepared for each of the patient terminals 1 and 10 and the doctor terminals 2-1 to 2-n, and then the history data be checked.

It is also preferable that the doctor terminals 2-1 to 2-n receive a manual designation for online or offline, wherein when offline is designated, a doctor be not called even when a call is made. Thus, a doctor can freely have the time for responding to emergency patients or patients coming to a hospital or the time for writing medical records.

It is also preferable that the online/offline set state of the doctor terminals 2-1 to 2-n be controlled by the patient terminal 1 or the healthcare support apparatus 120 and be referenced for selection of the destination. It is also preferable that the online/offline set state of the doctor terminals 2-1 to 2-n be displayed on the center terminal 3 so that the person in charge 8 can call a doctor efficiently.

It is also preferable that the center terminal 3 be called from the doctor terminals 2-1 to 2-n and a response to a message from the patient 6 be left up to the person in charge 8.

It is also preferable that, when the patient terminals 1 and 10 and the doctor terminals 2-1 to 2-n come into communication with each other, both or one of the patient terminals 1 and 10 and the doctor terminals 2-1 to 2-n record communication-history data such as communication destination, communication time, communication start/end time, communication contents (whether or not there are options such as calling of an ambulance).

Patient identification may be made in terminals 1 and 10 by using fingerprints, iris, voice, a password, and vital data.

Communication between the patient terminals 1, 10, and 130 and the doctor terminal 2, the center terminal 3, or the nurse terminal 100 may be achieved in various forms, such as by a general telephone, a TV telephone, an Internet telephone, and an e-mail.

Part of the elements of the first to third embodiments can be combined to another embodiment. For example, the healthcare support apparatus 120 according to the third embodiment may have the function of switching between the patient terminal 130 and the doctor terminal 2, the center terminal 3, or the nurse terminal 100, as in the second embodiment. The selecting procedure of the destination terminal in the first and second embodiments can be applied to the third embodiment; conversely, the selecting procedure of the destination terminal of the third embodiment can be applied to the first or second embodiment.

The assistant terminal is not necessarily the center terminal 3 and the nurse terminal 100 but may be a terminal used by other assistants such as a dietician.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of providing a healthcare support service with a healthcare support apparatus connectable to a plurality of providing-side terminals via a communication network, the method comprising:
   acquiring patient's vital signs data by a measuring device;
   determining whether or not the vital data contains an abnormal value;
   determining that messaging to a destination terminal is required by the patient when one of:
      a first case in which a messaging request is inputted by the patient into the healthcare support apparatus while the vital data contains an abnormal value, and
      a second case in which a messaging request is not inputted by the patient within a predetermined time after it is determined that the vital data contains the abnormal value;
   selecting, by a processor in the healthcare support apparatus, a destination terminal from the plurality of providing-side terminals according to whether the first case or the second case occurs; and
   transmitting a message to the selected destination terminal when it is determined that messaging to the selected destination terminal is required by the patient, the message being one of input by the patient, and generated for the patient depending on whether the first case or the second case occurs,
   wherein, in the selecting step, the destination terminal selected for the first case is different from the destination terminal selected for the second case,
   wherein when the plurality of providing-side terminals include assistant terminals different from doctor terminals, and
   wherein in the second case, the destination terminal selected in the selecting step is selected from among the assistant terminals.

2. The method according to claim 1, wherein the determination of whether or not the vital data contains an abnormal value is made by a criterion determined for each patient.

3. The method according to claim 1, wherein the determination of whether or not the vital data contains an abnormal value is made depending on a degree of change of the vital data.

4. The method according to claim 3, wherein the degree of change of the vital data is determined as a time integral and a vector value of the vital data.

5. The method according to claim 1, wherein when the messaging request is inputted by the patient and it is determined that the vital data contains the abnormal value, the destination terminal is selected from among the doctor terminals.

6. The method according to claim 1, wherein
   in the second case that the messaging is required by the patient because the messaging request is not inputted by the patient within the predetermined time after it is determined that the vital data contains the abnormal value, message information is transmitted to the destination terminal, the message information including information indicating that the message was automatically transmitted when the predetermined time passed, and
   in the first case that the messaging is required by the patient because the messaging request was inputted by the patient into the healthcare support apparatus while the vital data contained an abnormal value, message information is transmitted to the destination terminal, the message information indicating that the message information was transmitted based on an intention of the patient.

7. A healthcare support system including an apparatus connectable to a plurality of providing-side terminals via a communication network, the apparatus comprising:
   an input device configured to receive a messaging request from a patient;
   an acquisition unit configured to acquire patient's vital signs data;
   a first determination unit configured to determine the necessity of messaging to a destination terminal from the vital data acquired by the acquisition unit;
   a second determination unit configured to determine whether or not the vital data acquired by the acquisition unit contains an abnormal value, wherein
   the first determination unit determines that the messaging is required by the patient when one of:
      a first case in which a messaging request is inputted by the patient into the healthcare support apparatus while the vital data contains an abnormal value, and
      a second case in which a messaging request is not inputted by the patient within a predetermined time after it is determined that the vital data contains the abnormal value;
   a selection unit configured to select a destination terminal from the plurality of providing-side terminals according to whether the first case or the second case occurs; and
   a transmitting unit configured to transmit a message to the selected destination terminal when it is determined that messaging to the selected destination terminal is required by the patient, the message being one of input by the patient, and generated for the patient depending on whether the first case or the second case occurs,
   wherein, the selection unit is further configured to select the destination terminal selected for the first case different from the destination terminal selected for the second case,
   wherein the plurality of providing-side terminals include assistant terminals different from doctor terminals, and
   wherein in the second case, the selection unit is further configured to select the destination terminal from among the assistant terminals.

8. The healthcare support apparatus according to claim 7, wherein the second determination unit determines from a criterion determined for each patient whether or not the vital data contains an abnormal value.

9. The healthcare support apparatus according to claim 7, wherein the second determination unit determines whether or not the vital data contains an abnormal value depending on a degree of change of the vital data.

10. The healthcare support apparatus according to claim 9, wherein the degree of change of the vital data is determined as a time integral and a vector of the vital data.

11. The healthcare support apparatus according to claim 7, wherein:
   the selection unit selects the destination terminal from among the doctor terminals when the messaging request is inputted by the patient and it is determined that the vital data contains the abnormal value.

12. The healthcare support apparatus according to claim 7, wherein
   in the second case that the messaging is required by the patient because the messaging request is not inputted by the patient within the predetermined time after it is determined that the vital data contains the abnormal value, message information is transmitted to the destination terminal, the message information including information indicating that the message was automatically transmitted when the predetermined time passed, and
   in the first case that the messaging is required by the patient because the messaging request was inputted by the patient into the healthcare support apparatus while the vital data contained an abnormal value, message information is transmitted to the destination terminal, the message information indicating that the message information was transmitted based on an intention of the patient.

* * * * *